(12) United States Patent
Hedtke et al.

(10) Patent No.: US 7,986,921 B2
(45) Date of Patent: Jul. 26, 2011

(54) WIRELESS DEVICE WITH PRIVACY SCREEN

(75) Inventors: Paul Hedtke, San Diego, CA (US); Jack Steenstra, San Diego, CA (US); Kirk Taylor, San Diego, CA (US); Liren Chen, San Diego, CA (US); Yang Zhang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 1124 days.

(21) Appl. No.: 11/682,755

(22) Filed: Mar. 6, 2007

(65) Prior Publication Data

US 2008/0220814 A1    Sep. 11, 2008

(51) Int. Cl.
*H04B 1/38* (2006.01)
*H04M 1/00* (2006.01)

(52) U.S. Cl. ............ 455/90.3; 455/550.1; 455/566; 455/575.1; 455/575.3; 455/575.4

(58) Field of Classification Search ............ 455/90.3, 455/66.1, 404.1–404.2, 410–411, 414.1, 455/423–425, 418–419, 550.1, 552.1, 556.1–556.2, 455/557–559, 566, 575.1, 575.3–575.4, 575.6; 361/679.3–679.4, 679.21, 679.23, 679.26–679.29, 361/680, 730; 600/301, 307, 481, 485
See application file for complete search history.

(56) References Cited

U.S. PATENT DOCUMENTS

| | | | |
|---|---|---|---|
| 6,208,874 B1* | 3/2001 | Rudisill et al. | 455/550 |
| 6,950,647 B2* | 9/2005 | Ko | 455/411 |
| 2003/0050537 A1* | 3/2003 | Wessel | 600/300 |
| 2004/0125993 A1 | 7/2004 | Zhao et al. | |
| 2005/0060554 A1* | 3/2005 | O'Donoghue | 713/183 |
| 2005/0083642 A1* | 4/2005 | Senpuku et al. | 361/681 |
| 2005/0138356 A1* | 6/2005 | Hurwitz | 713/155 |
| 2005/0182366 A1* | 8/2005 | Vogt et al. | 604/131 |
| 2006/0061555 A1* | 3/2006 | Mullen | 345/169 |
| 2006/0252998 A1* | 11/2006 | Kimbrell | 600/300 |
| 2006/0284969 A1* | 12/2006 | Kim et al. | 348/14.01 |
| 2007/0013608 A1* | 1/2007 | Goo et al. | 345/1.1 |
| 2008/0004082 A1* | 1/2008 | Bloebaum | 455/566 |
| 2008/0139907 A1* | 6/2008 | Rao et al. | 600/323 |

FOREIGN PATENT DOCUMENTS

EP    1607822    12/2005

(Continued)

OTHER PUBLICATIONS

International Search Report—PCT/US08/055819, International Search Authority—European Patent Office—Aug. 4, 2008.

(Continued)

*Primary Examiner* — Meless N Zewdu
(74) *Attorney, Agent, or Firm* — James T. Hagler

(57) ABSTRACT

A cellular telephone including a medical device to monitor the medical or health condition of a user is provided. The cellular telephone is provided with a keypad that is movable from a first position, where a first display and keypad is exposed, to a second position where a second display and keypad is exposed. In the first position, the cellular telephone operates in a conventional cellular telephone manner. In the second position, the cellular telephone operates as the medical device. The second display and/or keypad is hidden from public view when the keypad is in the first position.

46 Claims, 6 Drawing Sheets

FOREIGN PATENT DOCUMENTS

| | | |
|---|---|---|
| EP | 1617631 | 1/2006 |
| GB | 2360904 | 10/2001 |
| KR | 19990063848 | 7/1999 |
| KR | 20050037903 A | 4/2005 |
| WO | 2005039065 | 4/2005 |

OTHER PUBLICATIONS

Written Opinion—PCT/US08/055819, International Search Authority—European Patent Office—Aug. 4, 2008.

* cited by examiner

WIRELESS DEVICE WITH PRIVACY SCREEN

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates generally to wireless devices, and more specifically to wireless devices having a movable keyboard to provide a privacy screen.

2. Background

Many people carry multiple electronic devices. These devices include cellular telephones, wireless laptop computers, pagers, wireless handheld computers, PDAs, handheld email units, such as, for example, a BLACKBERRY® from Research in Motion, and countless other electronic devices.

Some of the electronic devices are combinable. A BLACKBERRY® is an example of an electronic device that combines the functionality of a wireless email unit as well as a cellular telephone. Some electronic devices, however, relate to personal information, such as, for example, health information. While the electronics for the personal information can be combined with other electronic devices, the display of the information is typically relatively open and notorious to the public. For example, a wireless telephone could be combined with a blood glucose monitor, which is usable by, for example, diabetics. However, the cellular telephone display and keyboard would readily indicate to the public that the owner/user is diabetic. The owner/user of the telephone may wish to protect the personal information.

Thus, there exists in the art a need for a wireless device or handset having a privacy screen including a display and/or keyboard to allow access to information a user wishes to keep private such as, for example, health information.

SUMMARY

Embodiments disclosed herein address the above stated needs by providing a handset having a privacy screen for a display and/or keyboard. An aspect of the present application includes an electronic device with a housing. The housing contains a first display and a first component. The first component is movable connected to the housing such that the first component has a first position and a second position. A second display and second component also is contained in the housing, such that when the first component is in the first position, the second display and component are hidden and when the first component is in the second position, the second display and component are exposed.

In another aspect of the present application, a method of arranging an electronic device is provided. The method includes steps for accessing a second, private display associated with the electronic device. First, an electronic device in a first configuration is provided. The electronic device has a first input and a first, open display in the first configuration. Next, the first input is moved from the first configuration to the second configuration to expose a second, private display.

In yet another aspect of the present application, a wireless device that incorporates a personal medical monitoring device is provided. The wireless device may include a cellular telephone and a medical device to monitor vital statistics of a user and includes a housing that contains electronic circuits for operation of the cellular telephone and the medical device. A first input component associated with the cellular telephone is movably connected to the housing from a first position to a second position. A first, open display contained in the housing and being associated with the cellular telephone when the first input component is in the first position and a second, private display contained in the housing and being associated with the medical device when the first input component is in the second position.

The foregoing and other features, utilities, aspects and advantages of the device and system will be apparent from the following more particular description of a preferred embodiment of the invention as illustrated in the accompanying drawings.

DETAILED DESCRIPTION

The present technology will be described with reference to FIGS. 1-9. Although the following application specifically relates to combining the functionality of a cellular telephone with a blood glucose monitor, one of ordinary skill in the are will understand on reading the disclosure that other types of electronic devices could be combined. For example, other electronic devices include handheld computers, PDAs, pagers, oxygen monitors, pulse-ox monitors, blood pressure monitors, heart rate monitors, personal financial devices, or the like. Thus, the specific embodiment should be considered exemplary and non-limiting. The word "exemplary" is used herein to mean "serving as an example, instance, or illustration." Any embodiment described herein as "exemplary" is not necessarily to be construed as preferred or advantageous over other embodiments.

Figure 1:
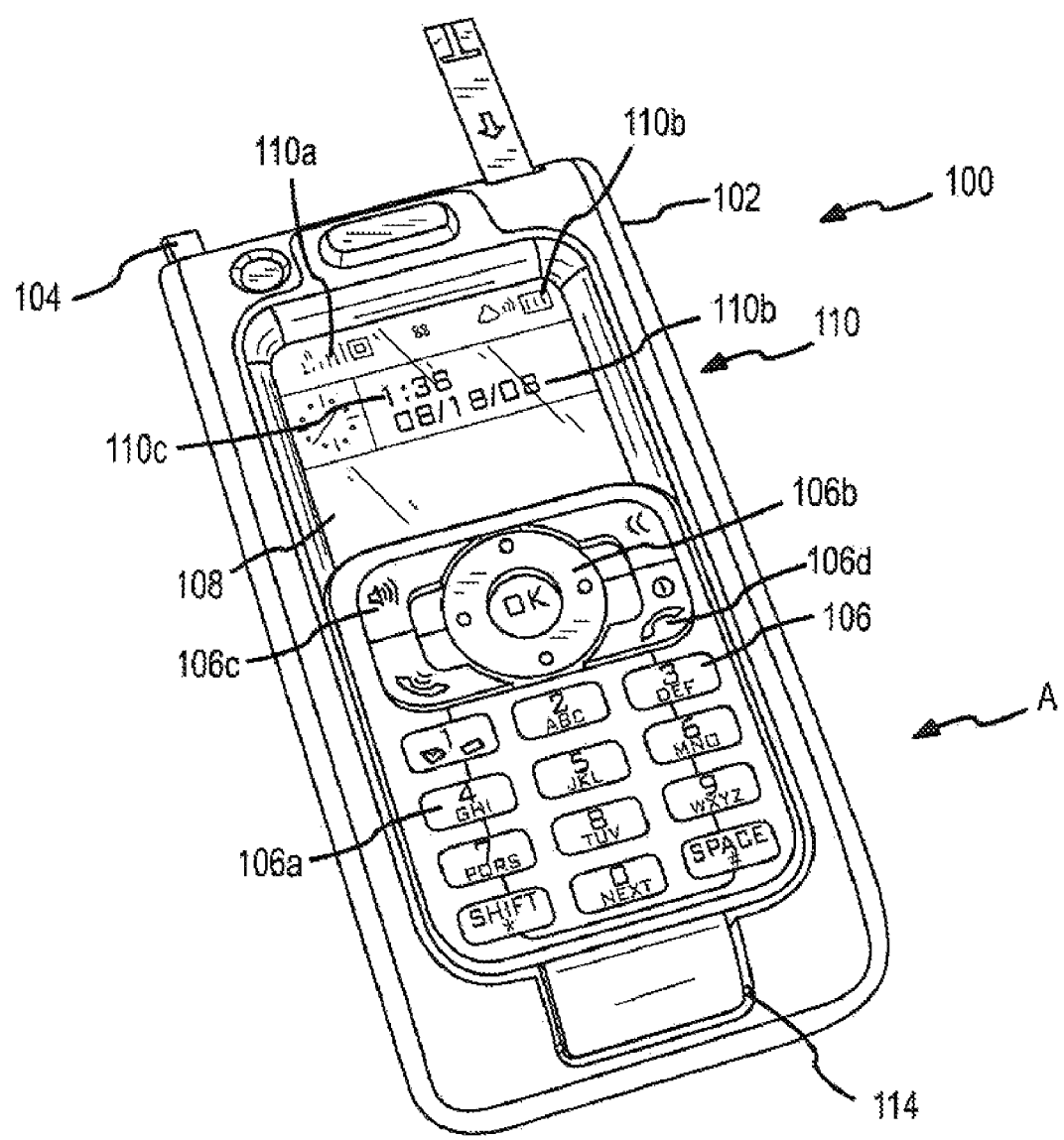
FIG. 1 is a front top perspective view of a wireless device incorporating technology associated with this application.

Referring now to FIG. 1, a handheld electronic device 100 is provided. Electronic device 100 is shown in a first configuration A, which may sometimes be referred to as the public or open configuration. Electronic device 100 in this example, as explained above, is a cellular telephone but could be any other electronic device, such as a PDA, handheld computer, or the like. Device 100 includes a housing 102 to contain the necessary electronic components software modules, and the like to perform the functionality of the electronic device. For a wireless device 100, an antenna 104 may be provided either internally or externally to device 100. Device 100 includes a first input component 106 and a first, open display 108. For a cellular telephone, first input component 106 is an alphanumeric keypad associated with a conventional cellular telephone. It includes numeric inputs 106a as well as a menu control button 106b, speaker and volume control 106c and the like. If electronic device was, for example, a handheld computer, first input component 106 may be more closely aligned with a conventional computer keyboard input.

First, open display 108 contains icons 110 associated with a cellular display panel. First, open display 108 may contain a graphical user interface. For example first, open display 108 includes icons 110 associated for radio frequency signal strength 110a, ring tone volume 110b, time 110c, and date 110d, or the like. Other icons are of course possible and the icon choice is largely a matter of design choice, functional particular, user desires and the like. Optionally, device 100 may have a cover panel (not specifically shown but generally understood in the art) to cover and/or protect first, open display and first input component 106 when not in use. One or the other inputs on first input component 106 would include a power button 106d for a user to turn power on and off. If the cover panel is used, the cover panel may interface with the power supply to shut down certain aspects of the unit when the cover panel is closed to conserve power.

Figure 4:
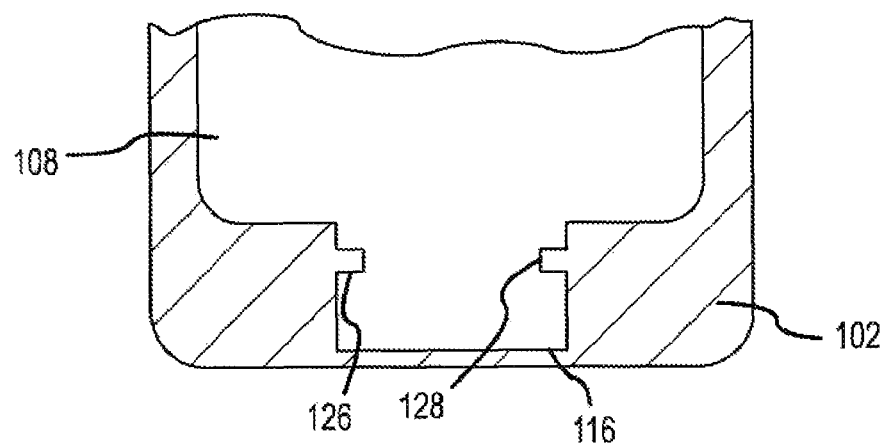
FIG. 4 is another cross-sectional view of a pivot associated with FIG. 1.
Figure 5:
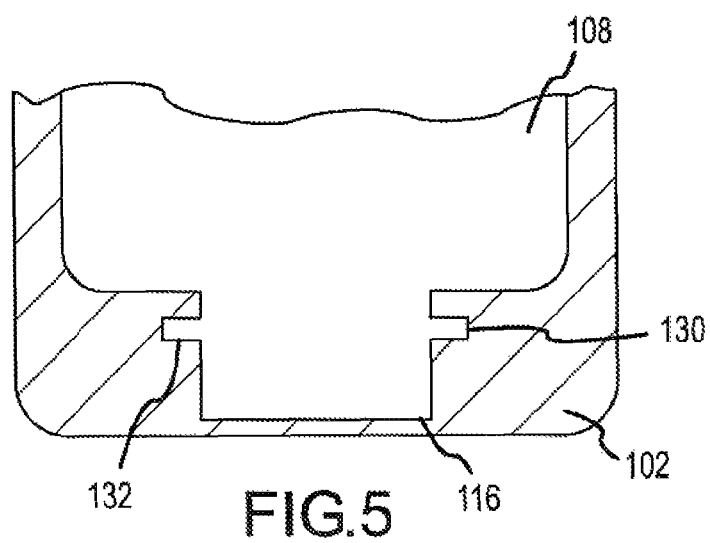
FIG. 5 is another cross-sectional view of a pivot associated with FIG. 1.

First input component 106 is pivotally connected to housing 102 at pivot 114. Pivot 114 is shown in cross-section in FIG. 3. Pivot 114 includes a recess 116 in housing 102. Recess 116 has walls 118 on either side with an axle 120 connecting the walls. First input component has a bore 122 through which axle 120 extends forming a rotatable or pivotable connection between housing 102 and first input component 106. While shown on a nominal bottom 124 of housing 102, pivot 114 could allow first input component 106 pivot and unfold in a down direction, up direction, left direction, right direction, or a combination thereof, such as, for example, a left and right direction by providing two pivots 114 such that the first input component 106 comprises a first half 106' and a second half 106" that open similar to window shutters. Instead of providing axle 120 extending across recess 116, axle 120 could be shaped more as protrusions 126 as shown in FIG. 4. In this case, bore 122 may be more akin to detents 128 or depressions instead of a through bore. Moreover, as shown in FIG. 5, the pivot connection may be reversed with protrusions 130 extending from first input component 106 into detents 132 on housing 102.

Figure 2:
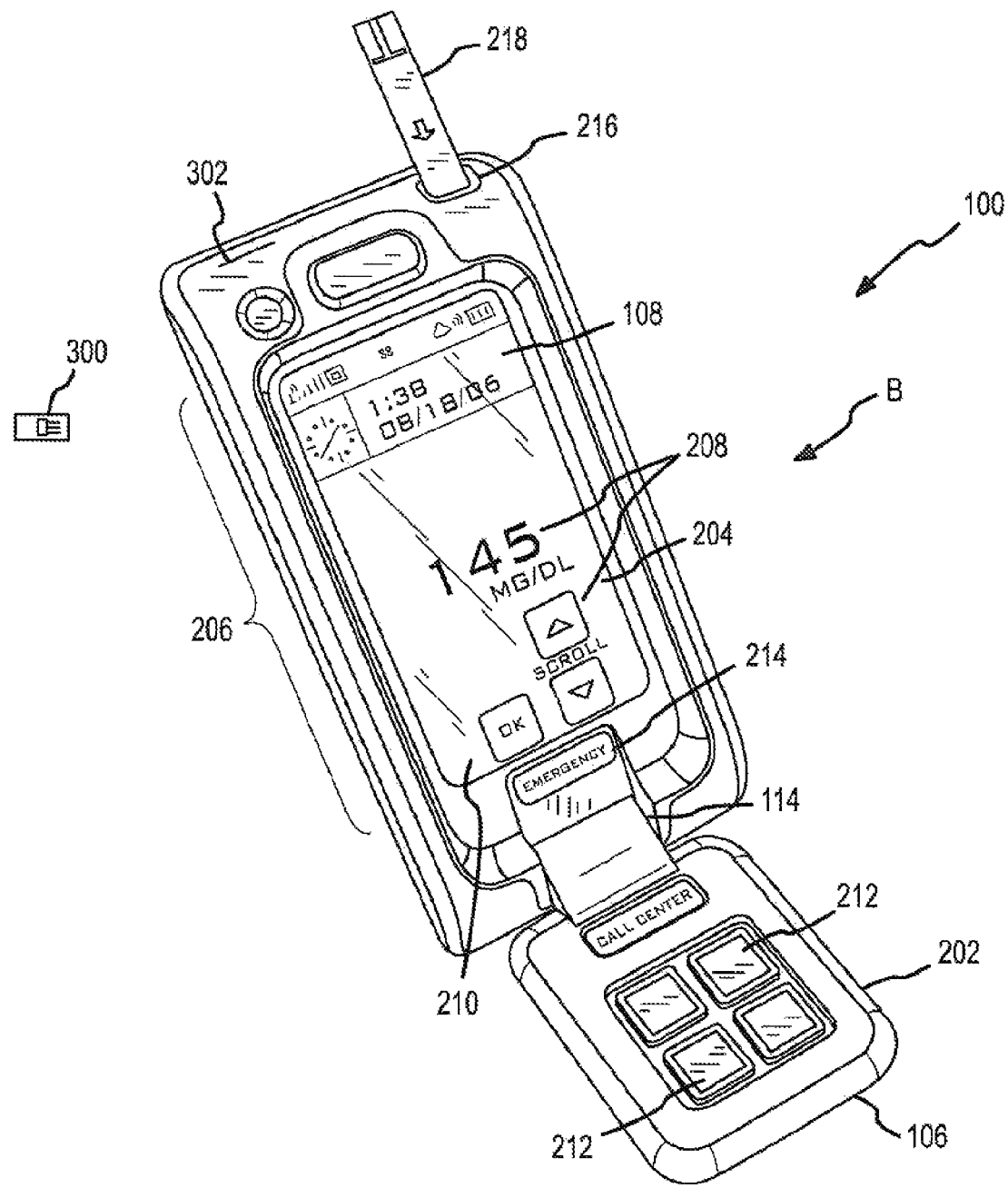
FIG. 2 is another front top perspective view of the wireless device of FIG. 1.
Figure 3:
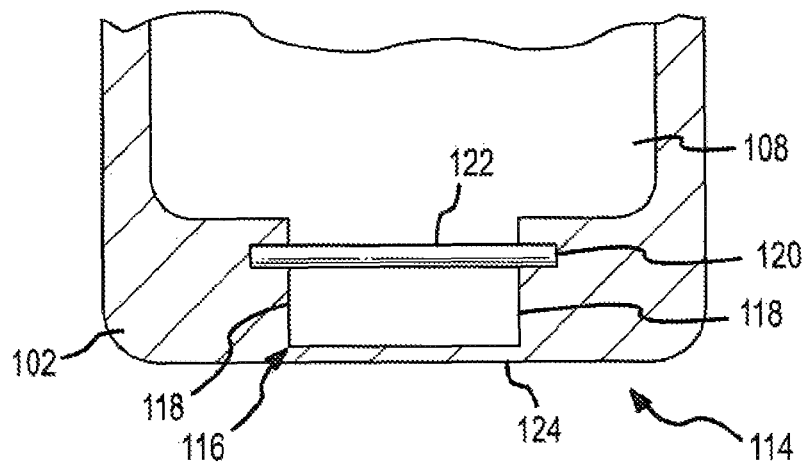
FIG. 3 is a cross-sectional view of a pivot associated with FIG. 1.

Referring now to FIG. 2, electronic device 100 is shown in a second configuration B, sometimes referred to as the private or closed configuration. In second configuration B, a second input component 202 is exposed by pivoting first input component 106 about pivot 114. As shown, second input component 202 is provided on a back surface of first input component 106. Although, depending on the application a second input component 202 may be unnecessary. Moreover, in second configuration B, a second, private display 204 is provided. Second, private display 204 was hidden by first input component 106 when in first configuration A. First, open display 108 and second, private display 204 can be contiguous to form a combined display 206 as shown. Alternatively, second, private display 204 may be a stand-alone display, see FIG. 9. Display 204 or combined display 206 would contain icons 208 related to the functionality of the second electronic device contained in device 100. As shown, electronic device 100 provides a blood glucose monitor graphical user interface 210. Second input component 202 similarly comprises keys 212 relevant to the appropriate functionality. As the present device 100 combines the functionality of a blood glucose monitor, it may have an emergency interlock 214 to alert emergency medical personnel should a dangerous medical condition be detected. As shown interlock 214 is provided as push button, but other types of interlocks are possible.

In conjunction with device 100, housing 102 may have an input port 216 to receive, for example, biological specimens. In this case, a drop of blood may be inserted using a sample tab 218 that fits in input port 216. Electronic device 100 would read the biological specimen and provide the appropriate indication on second, private display 204. Other styles or input ports could accept electrical inputs instead of physical inputs. For example, input part 216 may accept reading from a heart rate monitor, a pulse-ox monitor, a blood pressure monitor, etc.

As information displayed on second, private display 204 is potentially personal information, it is possible to provide password protection prior to allowing second, private display 204 to display any information. Alternatively, pivot 114 may be interlocked with a password or have a key 300 insertable into a lock 302.

Figure 6:
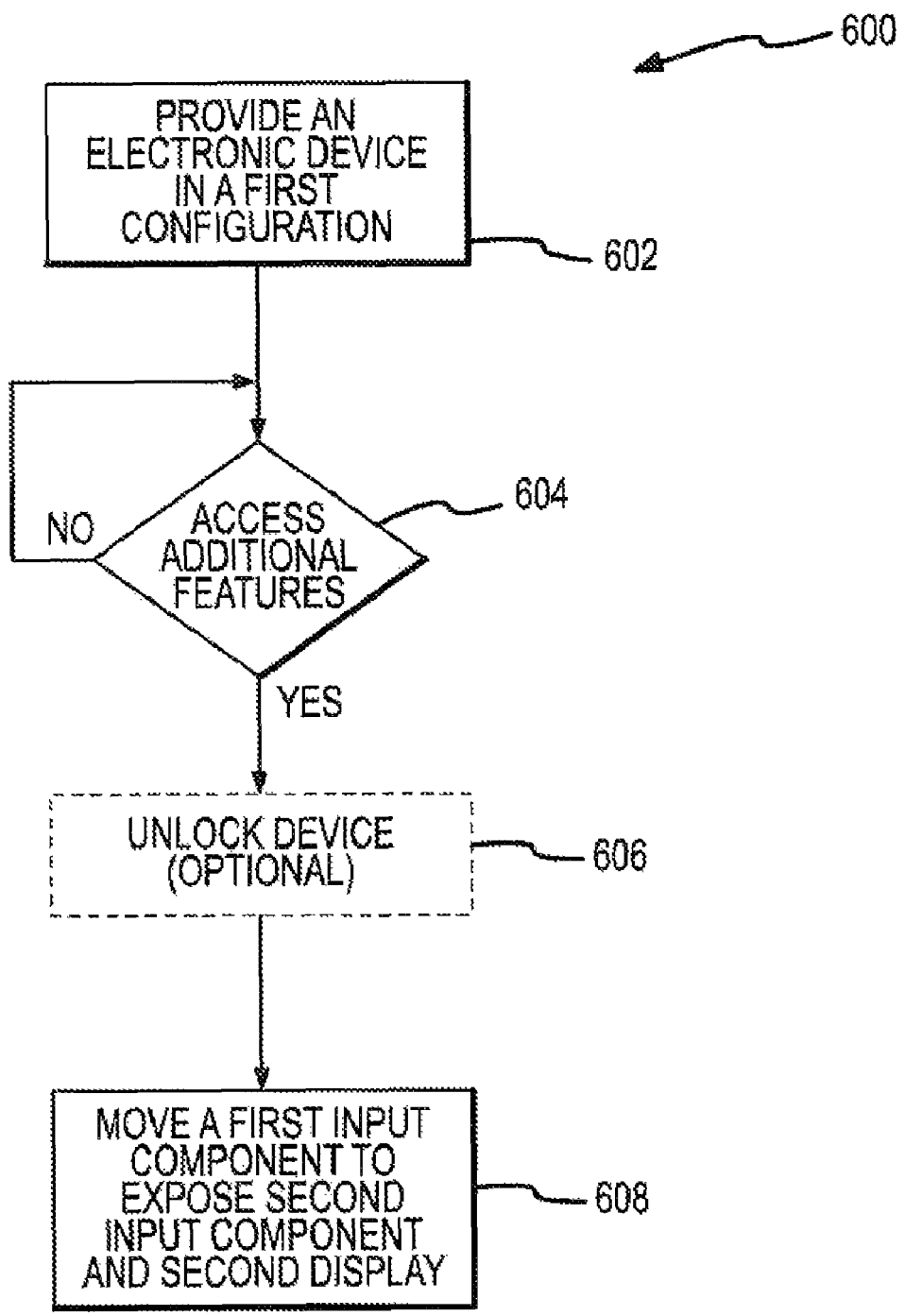
FIG. 6 is a flowchart illustrating one method of operating the electronic device of FIG. 1.

Referring now to FIG. 6, a flowchart 600 is provided illustrating a potential method of operating electronic device 100. While flowchart 600 is provided with a series of steps, these steps can be interchanged or substituted without departing from the scope of use of the electronic device. Moreover, steps show as separate for convenience may be combined into a single step. Also, a single step may be broken into a series of two or more steps. First, an electronic device in a first configuration A is provided, step 602. In first configuration A, a first input component is exposed and available for use. Moreover, a first, public display is observable. Next, a decision is made to access the features of device 100 not available using first, public display and/or first input component, step 604. Optionally, a lock preventing accessing the second input component and/or second, private display is disabled, step 606. The lock could be, for example, an electronic interlock or mechanical lock. The lock may be disabled via a password, biometric signature (such as a thumb print, retina scan, voice print, or the like), a key or key card, or the like. Next, the first input component is moved such that a second input component is exposed, step 608. Substantially simultaneously, second, private display is exposed as well. Thus, electronic device 100 is provided in a second configuration B.

Figure 7:
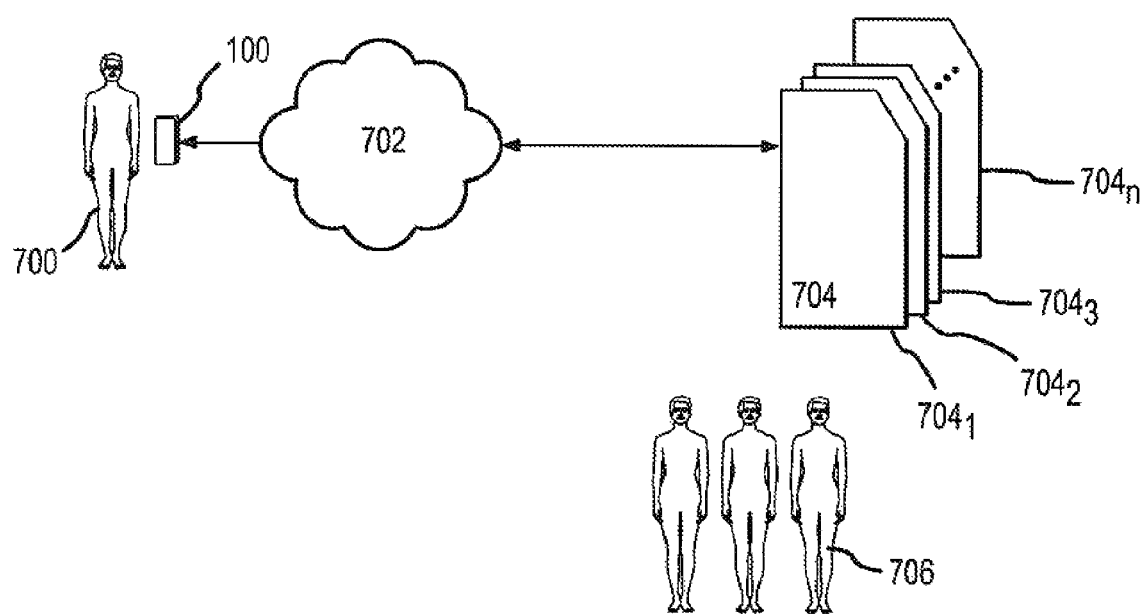
FIG. 7 is a system incorporating technology associated with this application.

As can be appreciated, electronic device 100 as a cellular telephone provides a mechanism to transmit health related data obtained by a personal medical device to a central repository. The cellular telephone transmission protocols provide a HIPAA or other regulatory complaint mechanism to transmit the data although controls would need to be established on a repository server to avoid violation of HIPAA. Referring now to FIG. 7, a user 700 of electronic device 100 is shown. In this example, medical information detected by device 100 would be transmitted over cellular network 702 to central repository 704. Central repository 704 could be a single facility or a series of networked facilities $704_{1-n}$. While shown as a cellular telephone transmitting medical information using cellular telephone protocols, other networked transmissions are possible including both wired and wireless networks. Medical staff 706 could review the medical information at central repository 704 on a scheduled or random basis to provide medical instructions or health tips to user 700. Moreover, alarm conditions in central repository 704 could alert medical staff 706 of a potential health risk to user 700, which would allow medical staff 706 to act in a more expedited manner. Such emergency service may include contacting local "911" services or the like.

Figure 8:
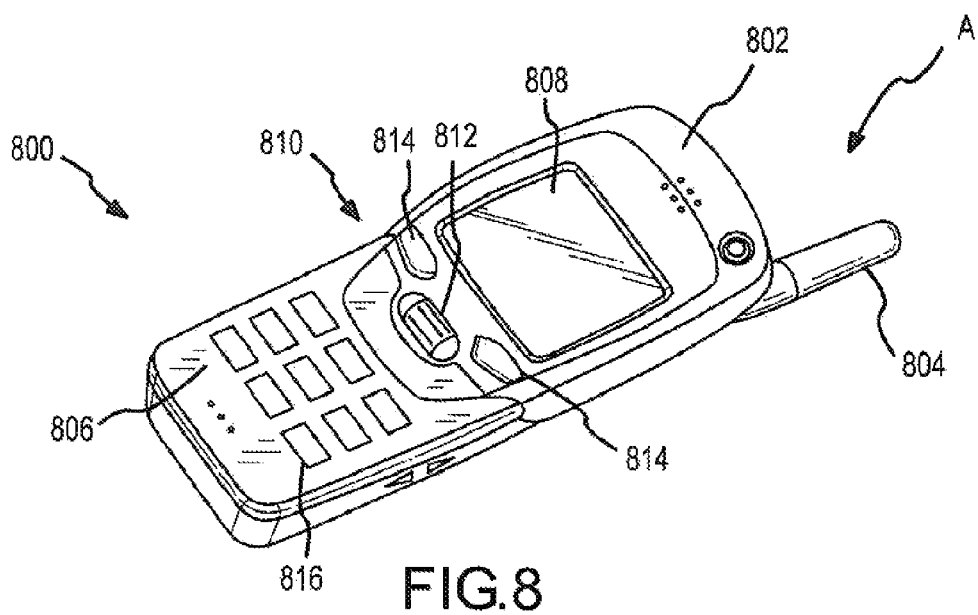
FIG. 8 is a perspective view of a wireless device incorporating technology associated with this application.
Figure 9:
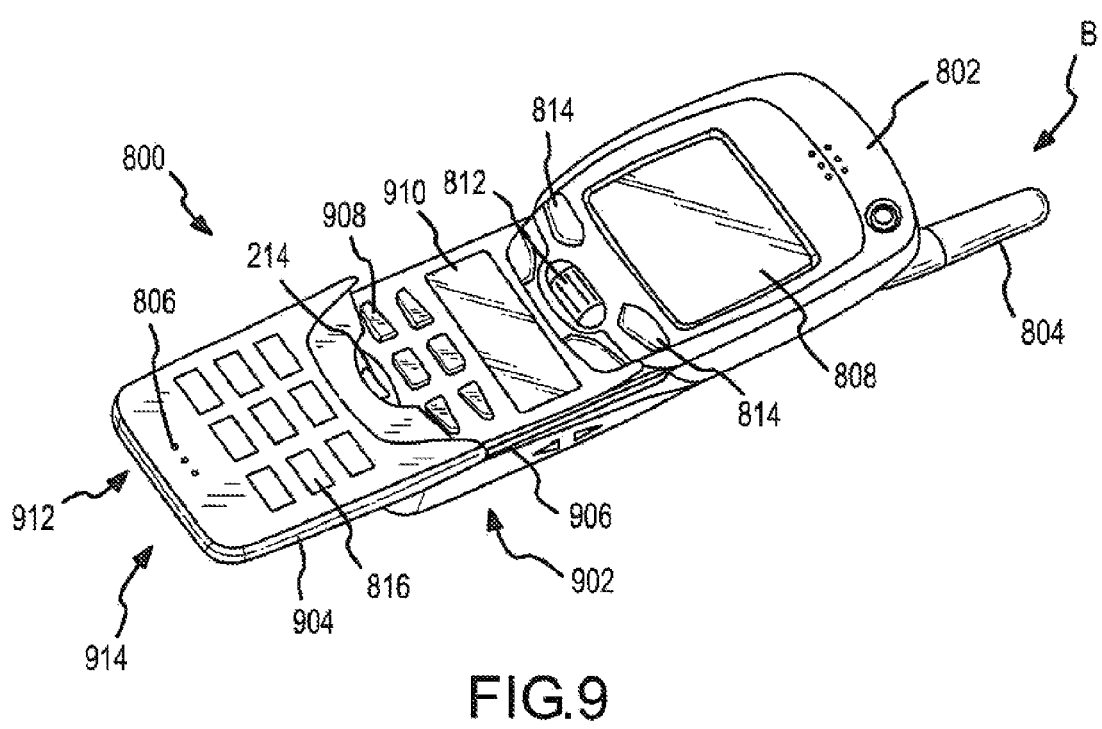
FIG. 9 is another perspective view of the wireless device of FIG. 8.

FIGS. 1-7 have described exemplary embodiments of the technology associated with a pivot or clam shell style wireless device. One of ordinary skill in the art on reading the disclosure, however, would understand other styles of wireless device configurations are possible, such as, for example, slider or wrap around devices. Referring specifically to FIGS. 8 and 9, a slider style wireless device 800 is provided as an exemplary embodiment. Wireless device 800 is shown as a cellular telephone, but could be, for example, a handheld computer, a digital music player, or a PDA to name but a few. Wireless device 800 in FIG. 8 is shown in a first configuration A. Device 800 includes a housing 802, an antenna 804, a first input component 806 and a first, open display 808. First input component 806 contains keys 816 to allow a use to access and use device 800's features. Device 800 may be provided with a separate cover (not shown, but which may be a slider style, clam shell style, wrap around style, or the like). Device 800 also may have some specialty buttons 810, such as, for example, a menu button 812, selection control buttons 814, or the like. Moreover, display 808 may contain icons consistent with the designed use of device 800.

FIG. 9 shows device 800 is a configuration B. In configuration B, first input component 806 has been moved along slide connection 902, which consists of a rail 904 on first component 806 in a groove 906 on housing 802. Moving first input component 806 into configuration B exposes second input component 908 and second, private display 910. Although instead of a separate second, private display 910, moving first input component 806 into configuration B may provide an interlock to switch first, open display 808 to a second, private configuration. Moreover, first input component may also pivot to expose a third input component 912 that resides on a back side 914 of first input component 806. Similar to device 100, device 800 also may have an interlock to prevent access of the private portions of the device, a emergency contact or panic button 214, or the like.

The previous description of the disclosed embodiments is provided to enable any person skilled in the art to make or use the technology of the present application. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An electronic device, comprising:
   a housing;
   a first display contained in the housing;
   a first input component contained in the housing, the first input component being movably connected to the housing and having a first position and a second position;
   a second display contained in the housing; and
   a second input component contained in the housing, wherein:
      the first display and the first input component are exposed when the first input component is in the first position; and
      the second display and the second input component are hidden when the first input component is in the first position and exposed when the first input component is in the second position.

2. The electronic device according to claim 1, usable as a cellular telephone when the first component is in the first position.

3. The electronic device according to claim 1, usable to monitor a medical condition of a user when the first component is in the second position.

4. The electronic device according to claim 1, wherein the first component is pivotally connected to the housing.

5. The electronic device according to claim 1, wherein the first component is slidably connected to the housing.

6. The electronic device according to claim 5, wherein the first component is pivotable to expose a third component.

7. The electronic device according to claim 1, wherein access to the second display requires disabling a lock.

8. The electronic device according to claim 7, wherein the lock requires a password to access the second display.

9. The electronic device according to claim 7, wherein the lock requires a biometric to access the second display.

10. The electronic device according to claim 7, wherein the lock requires a key.

11. The electronic device according to claim 3, further comprising an input port contained in the housing to receive biological specimens.

12. The electronic device according to claim 1, wherein the electronic device is a cellular telephone.

13. The electronic device according to claim 1, wherein the electronic device is a medical instrument.

14. The electronic device according to claim 12, wherein the electronic device also is a medical instrument.

15. The electronic device according to claim 13, wherein the medical instrument is selected from a group of medical instruments consisting of a blood glucose monitor, a heart rate monitor, a variable heart rate monitor, a blood pressure monitor, an oxygen monitor, a pulse-ox monitor, and a temperature monitor.

16. The electronic device according to claim 1, wherein the second input component resides on a back of the first component.

17. A method for accessing a private second display on an electronic device, comprising the steps of:
   providing an electronic device in a first configuration, the first configuration having at least a first input component and an open first display, wherein the first input component is movably connected to a housing such that the first input component has a first position and a second position; and
   moving the first input component such that the electronic device is in a second configuration wherein a private second display and a second input component are exposed,
   wherein the private second display and the second input component are hidden when the first input component is in the first position.

18. The method of claim 17, wherein the step of moving the first input component comprises pivoting the first input component relative to the electronic device.

19. The method of claim 17, wherein the step of moving the first input component comprises sliding the first input component relative to the electronic device.

20. The method of claim 17, further comprising a step of unlocking the device.

21. The method of claim 20, wherein the step of unlocking includes entering a password.

22. The method of claim 20, wherein the step of unlocking includes receiving a biometric.

23. The method of claim 20, wherein the step of unlocking includes inserting a key.

24. The method of claim 17, wherein the step of moving the first input component includes the step of exposing the second input component.

25. A wireless electronic device comprising at least a cellular telephone and a medical device to monitor a user, the wireless electronic device comprising:
a housing;
electronic circuits for the cellular telephone and the medical device contained within the housing;
a first input component, the first input component being movably connected to the housing and having a first position and a second position;
an open first display contained in the housing and being associated with the cellular telephone when the first input component is in the first position,
a private second display contained in the housing and being associated with the medical device when the first input component is in the second position; and
a second input component associated with the medical device, wherein the private second display and the second input component are hidden when the first input component is in the first position and exposed when the first component is in the second position.

26. The wireless electronic device of claim 25, wherein the medical device is selected from a group of medical devices consisting of a blood glucose monitor, a heart rate monitor, a variable heart rate monitor, a blood pressure monitor, an oxygen monitor, a pulse-ox monitor, and a temperature monitor.

27. The wireless electronic device of claim 25, further comprising a specimen input port.

28. The wireless electronic device of claim 25, wherein the second input component resides on a back of the first input component.

29. The wireless electronic device of claim 25, further comprising an interlock to inhibit access to the private second display.

30. The wireless electronic device of claim 29, wherein the interlock locks the first input component in the first position.

31. The wireless electronic device of claim 29, wherein the interlock is unlocked using a biometric.

32. The wireless electronic device of claim 29, wherein the interlock is unlocked using a password.

33. The wireless electronic device of claim 29, wherein the interlock is unlocked using a key.

34. The wireless electronic device of claim 25, further comprising an emergency interlock to transmit an emergency signal.

35. The wireless electronic device of claim 25, wherein the open first display and the private second display are contiguous.

36. A system associated with medical information of a user, comprising:
a mobile device connected to a central repository over a network, wherein the mobile device is configured to communicate the user's medical information to the central repository,
wherein the mobile device comprises:
a medical device configured to measure the medical information of the user;
a housing;
a first input component coupled to the housing and having a first position and a second position;
an open first display contained in the housing;
a private second display; and
a second input component associated with the medical device,
wherein the private second display and the second input component are hidden when the first component is in the first position and exposed when the first input component is in the second position.

37. The system of claim 36, wherein medical staff reviews the medical information and communicates the information to the user over the network.

38. The system of claim 36, wherein the central repository provides emergency services on an alarm condition.

39. An electronic device, comprising:
a first display;
a first input component;
means for providing a first configuration of the electronic device; and
means for providing a second configuration of the electronic device,
wherein:
the means for providing the first configuration comprises the means for exposing the first display and a first input component and means for hiding a private second display and a second input component; and
the means for providing the second configuration comprises the means for moving the first input component such that the private second display and the second input component are exposed.

40. The electronic device of claim 39, wherein the means for moving the first input component comprises means for pivoting the first input component relative to the electronic device.

41. The electronic device of claim 39, wherein the means for moving the first input component comprises means for sliding the first input component relative to the electronic device.

42. The electronic device of claim 39, further comprising means for unlocking the device.

43. The electronic device of claim 42, wherein the means for unlocking includes means for entering a password.

44. The electronic device of claim 42, wherein the means for unlocking includes means for receiving a biometric.

45. The electronic device of claim 42, wherein the means for unlocking includes means for inserting a key.

46. The electronic device of claim 39, wherein the means for moving the first input component includes means for exposing the second input component.

* * * * *